United States Patent [19]

Shapiro

[11] 4,249,825

[45] Feb. 10, 1981

[54] METHOD AND APPARATUS SUITABLE FOR OCULAR BLOOD FLOW ANALYSIS

[75] Inventor: Jerrold M. Shapiro, Natick, Mass.

[73] Assignee: The Trustees of Boston University, Boston, Mass.

[21] Appl. No.: 38,610

[22] Filed: May 14, 1979

[51] Int. Cl.³ .............................................. G01J 1/42
[52] U.S. Cl. .................................. 356/223; 128/654; 128/745
[58] Field of Search .......................... 356/223; 354/20; 128/654, 745

[56] References Cited

PUBLICATIONS

Ben-Sira, I and Riva, C., "Fluorophotometric Recording of Fluoroscein Dilution Curves in Human Retinal Vessels", *Investigative Ophthalmology*, vol. 12, No. 4, Apr. 1973, pp. 310-312.
Bullpitt, C. J. and Dollery, C. T., "Estimation of Retinal Blood Flow by Measurement of the Mean Circulation Time," *Cardiovascular Research*, vol. 5, pp. 406-412 (1971).
Fonda, S. and Bagolini, B., "Relative Photometric Measurements of Retinal Circulation (Dromofluorograms)", *Arch. Opthalmology*, vol. 95, Feb. 1977, pp. 302-307.
Hickam, J. B. and Frayser, R., "A Photographic Method for Measuring the Main Retinal Circulation Time Using Fluoroscein," *Investigative Opthalmology*, vol. 4, Oct. 1965, pp. 876-884.
Hickam, J. B. and Frayser, R., "Observations on Vessel Diameter, Arteriovenous Oxygen Difference and Mean Circulation Time," *Circulation*, vol. XXXIII, Feb. 1966, pp. 302-316.
Read, J. S. et al., "Measurement of Mean Retinal Circulation Time with a Computer-Controlled Television Ophthalmoscope Image Processor," Arvo Abstract, p. 226.
Riva, C. E. et al., "Fluoroscein Dye-Dilution Technique and Retinal Circulation," Am. J. Physiol. 243(3): H315-H433, 1978.

*Primary Examiner*—John K. Corbin
*Assistant Examiner*—Bruce Y. Arnold
*Attorney, Agent, or Firm*—Hamilton, Brook, Smith & Reynolds

[57] ABSTRACT

Glaucoma and other diseases may be detected by the analysis of angiograms to determine ocular blood flow. Using rapid sequence photography an ocular image is recorded on successive film frames. To determine the optical density of the film at selected image sites, the image position on the frames being subject to change from frame to frame, each frame is initially positioned manually at a starting position relative to a density sensing system. Then, X-Y stepping motors move the film under control of a digital processor to position the film frame at each selected image site. A detector is insensitive to light from a viewing optical system because of a filter included in that system. A crosshair image-point indicator is included on a filter in the viewing system.

17 Claims, 8 Drawing Figures

METHOD AND APPARATUS SUITABLE FOR OCULAR BLOOD FLOW ANALYSIS

GOVERNMENT SPONSORSHIP

Work relating to this invention was supported by Grant No. 5RO1EYO17788-03 from the National Institute of Health.

DESCRIPTION

Technical Field

This invention relates to the analysis of recorded images to determine optical density at predetermined locations in the images. The invention is particularly applicable to the analysis of ocular angiograms to provide blood flow data. The angiograms may provide an indication of glaucoma.

BACKGROUND ART

The shape of the normal eye is maintained by an internal fluid pressure of about 15 mm of mercury. That intraocular pressure (IOP) is controlled by the balance of flow of aqueous humor due to secretion from the ciliary body and drainage through the trabecular meshwork. In the disease of glaucoma, the balance is disturbed. The result is an increase in IOP which forces the retina outwardly to squeeze the choroid against the fairly inelastic sclera.

Blood flow in the choroid is related to the perfusion pressure, the difference between the mean arterial blood pressure outside the eye and the IOP. Thus an increase in IOP decreases the perfusion pressure and reduces the blood supply to the choroid. The peripapillary choroid near the optic nerve is most sensitive to a decrease in perfusion pressure. That portion of the choroid supplies blood to the intraocular part of the optic nerve (the optic disc), and an increase in IOP may reduce optic disc blood flow sufficiently to cause blindness.

The most widely used test for glaucoma has been a measurement of the IOP. However, the IOP which results in the earliest loss of vision varies widely from patient to patient. Thus measurement of IOP alone is not adequate to predict whether an eye will progress toward visual loss. It has been suggested that a better means for testing for glaucoma is to monitor the blood flow in the choroid.

Fluorescein angiography is widely used by ophthamologists for qualitatively examining the circulatory systems of the eye. Several cubic centimeters of fluorescein dye are rapidly injected as a bolus into a vein, and the transit of the dye through the eye's blood vessels is followed using rapid sequence photography. The dye is excited by blue light to fluoresce a bright yellow-green. Filters in a fundus camera block the blue exciting light so that the resulting film negatives are only exposed at the portions of the ocular image corresponding to fluorescent, dye-filled blood vessels. The film can be calibrated to provide an indication of the intensity of the fluorescent light striking the film at any given location. That information is made a function of time by precisely timing each of the rapid sequence photographic frames. By thus determining the time of arrival of the dye in various ocular tissues, one can determine whether the blood flow has been altered by disease.

Fundus cameras capable of providing a timed rapid sequence of ocular image frames are well known. Problems have occurred, however, in the extraction of data from the images. The usual approach has been to manually locate an intensity sensing system relative to a point on the image. For a given frame the intensity sensing system is moved to ten or more predetermined sites. Each frame of the sequence is similarly examined at the same sites. In laboratory studies, the eye of a test animal must be examined at the same sites on a day-to-day basis. Although those locations can be selected at convenient locations on the image, it has been found that operators are not able to remember more than a few locations and are thus unable to rapidly position the intensity sensing system at the several locations on each image frame.

An object of this invention is to provide automatic location of the intensity sensing system relative to the ocular fundus image.

Because the eye does not remain stationary through the entire sequence, the image moves relative to the film or television frames throughout the sequence. This greatly complicates automatic positioning of the intensity sensing system at many predetermined locations in a complicated network of ocular blood vessels. Thus, a further object of the invention is to provide such a system which is substantially automatic yet which is not affected by movement of the image on successive image frames.

By meeting the above objects of this invention a method is provided for obtaining a large quantity of data regarding the ocular blood flow of a patient.

DISCLOSURE OF THE INVENTION

In accordance with the invention in one of its aspects, a plurality of image frames are provided, each frame having been taken at a known instant. To determine the optical density of the image at the same preselected image locations on successive frames, each image frame is positioned at a starting position relative to an intensity sensing system. The image frame and intensity sensing system are then moved relative to each other under electronic control to sense additional predetermined image sites. The electronic control may be independent of the sensed image once positions are in memory.

In accordance with the invention in another of its aspects, the image is formed on a sequence of film frames. An optical system illuminates the film on a carrier and projects the light from an illuminated point of the image frame onto a photodetector. Drive control means for moving the film and optical system relative to each other includes a control data memory. The stored control data establishes sites relative to the starting position of the film frames.

In accordance with the invention is another of its aspects, a detector detects a passband of light frequencies. A sensing optical system illuminates a selected image point on the film and directs the light from that point to the detector. A viewer optical system illuminates a complete image on the film and directs the light from the image to a viewer. This viewer optical system includes a filter ahead of the film for filtering a stopband of frequencies from the image illuminating light. The stopband coincides with the detector passband.

In accordance with a preferred form of the invention, at each predetermined site of the image the intensity sensing system scans the image. The minimum or maximum intensity sensed during the scan is then stored as test data.

Also in accordance with a preferred form of the invention, a film carrier is moved by X/Y stepping motors. The stepping motors may be controlled manually to first position the sensing system at each of the predetermined image sites to enable storage of those sites in the control memory. The manual control may also be used to set the sensing system at the starting position.

Preferably, the automatic control of the system from the image starting position is by means of a digital processor.

In a preferred use of the invention, ocular blood flow data is obtained. That data can then be used to detect such diseases as glaucoma. In a particularly advantageous form of the invention the delay time for blood to arrive at some portions of the eye such as the optic disc after blood has arrived at the central retinal artery, is derived.

BRIEF DESCRIPTION OF THE DRAWINGS

The foregoing and other objects, features and advantages of the invention will be apparent from the following more particular description of a preferred embodiment of the invention, as illustrated in the accompanying drawings in which like reference characters refer to the same parts throughout the different views. The drawings are not necessarily to scale, emphasis instead being placed upon illustrating the principles of the invention.

BEST MODE OF CARRYING OUT THE INVENTION

Figure 1:
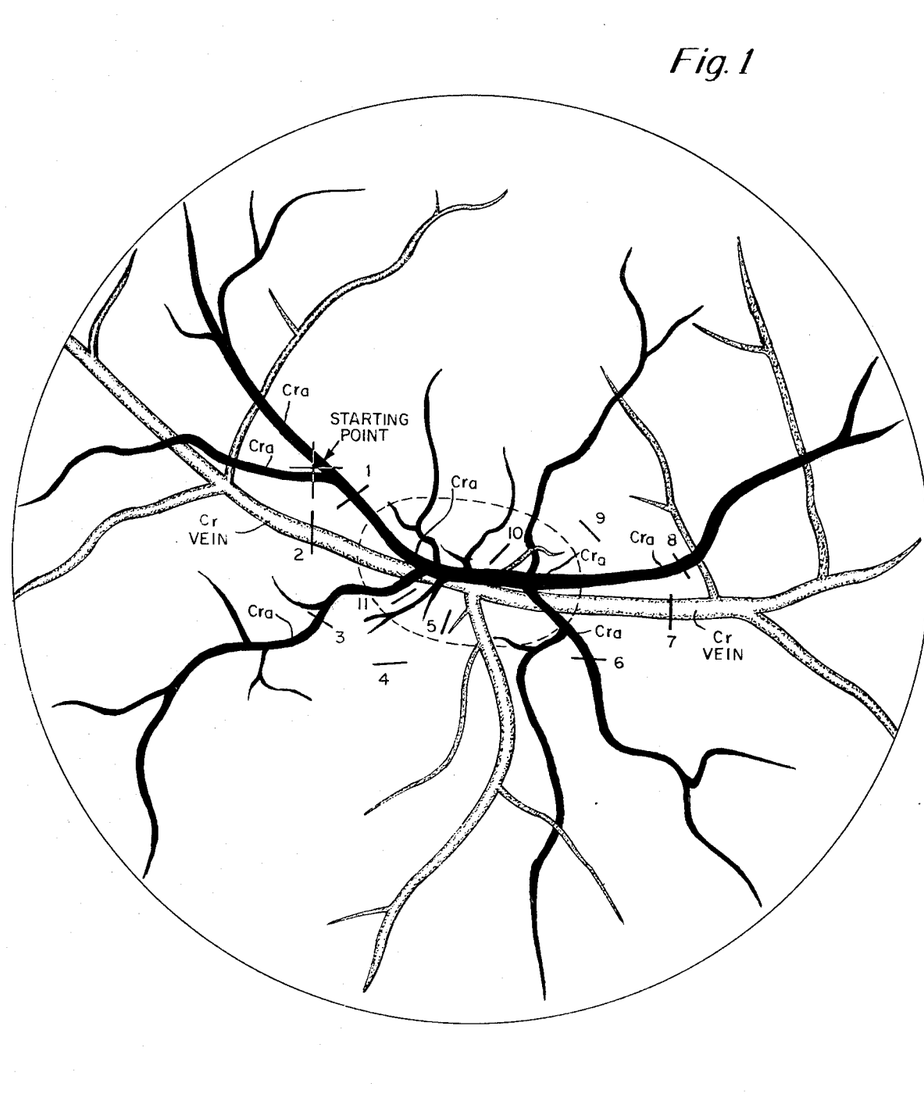
FIG. 1 is an illustration of an ocular fundus image recorded by means of a fundus camera.

As noted above, a fundus camera (not shown) is positioned to illuminate the back wall (fundus) of the eye and to record the flow of dye through the blood vessels with rapid sequence exposures. Such an exposure is illustrated in FIG. 1. Although a negative image is used, a positive image is an alternative. The image includes a network of central retinal arteries (cra) and central retinal veins (crv). In the veins, the dye intensity is greatest along the walls due to laminar flow in the veins. In the arteries, however, the dye is most dense at the center of a vessel.

The optic disc is in the area indicated by the broken lines in FIG. 1. The choroid and retina are in layers outside of the optic disc. The retina is the innermost layer and can be readily seen in a fundus photograph. The choroid is behind the retina and other layers including the pigment epithelium. Dye flowing through the choroid is seen as a glow rather than as the distinct vessels shown in the retina.

With the present system, a timed sequence of image frames is analyzed to determine the time of arrival of dye in various retinal vessels as well as the time of arrival in the choroid and optic disc. For that purpose, a number of image sites are selected and the density of each frame at each of the selected sites is determined. The time of arrival of the dye at any site is taken as the time of the frame having maximum dye concentration at that site.

In the image of FIG. 1, eleven image sites have been selected. Sites 1, 3, 6 and 8 span central retinal arteries; sites 2 and 7 span central retinal veins; sites 5, 10 and 11 are located on the optic disc away from the retinal arteries and veins; and sites 4 and 9 are positioned over the retina away from the retinal arteries and veins. The sites 4 and 9 can be used to sense the glow from the choroid as dye passes therethrough.

An intensity sensing system to be described subsequently is successively positioned over each site of each frame automatically. At each site, the system is caused to scan in a predetermined direction. The maximum dye concentration noted during that scan is taken as the datum for that location. That datum is an indication of the intensity of light transmitted through the film point and thus of the density of the film at that point. The density is in turn indicative of fluorescent intensity. By plotting intensity (or density) against time for each site, the time of arrival of the dye, defined as the time of maximum concentration of the dye, can be calculated.

For a patient or test animal suffering from glaucoma, the time of arrival of the dye at sites 5, 10 and 11 will be delayed or nonexistant because of the restricted flow to the optic disc. The flow through the retinal vessels is substantially unaffected by the increased IOP, and the time of arrival of the dye in the central retinal arteries can be used as a reference time. A delay time d can then be defined as $$d = t_p - t_{cra} \qquad (1)$$

where $t_p$ is the time of arrival of dye on the optic disc or peripapillary choroid and $t_{cra}$ is the time of arrival of dye at the central retinal artery. Because the time $t_{cra}$ is substantially unchanged by increases in IOP, the delay time d may be an accurate indication of the flow restriction through the choroid and optic disc. That in turn is an accurate indication of the extent to which the patient suffers from glaucoma.

Because the eye moves somewhat throughout the imaging sequence and from one sequence to the next, one cannot select sites using the photographic frame boundary as a reference and still except to sense corresponding points of the ocular fundus on each image frame. Thus, in order to provide automatic control, with the present method an operator selects a starting point on the fundus image. The starting point is selected to serve as an easy reference in aligning each frame to be analyzed. Then, the operator stores the coordinates of each site on the image relative to that starting point. Those coordinates can be stored in the memory of a microprocesser and can be recalled to automatically position each image frame for sensing optical density at the same preselected image sites.

Figure 2:
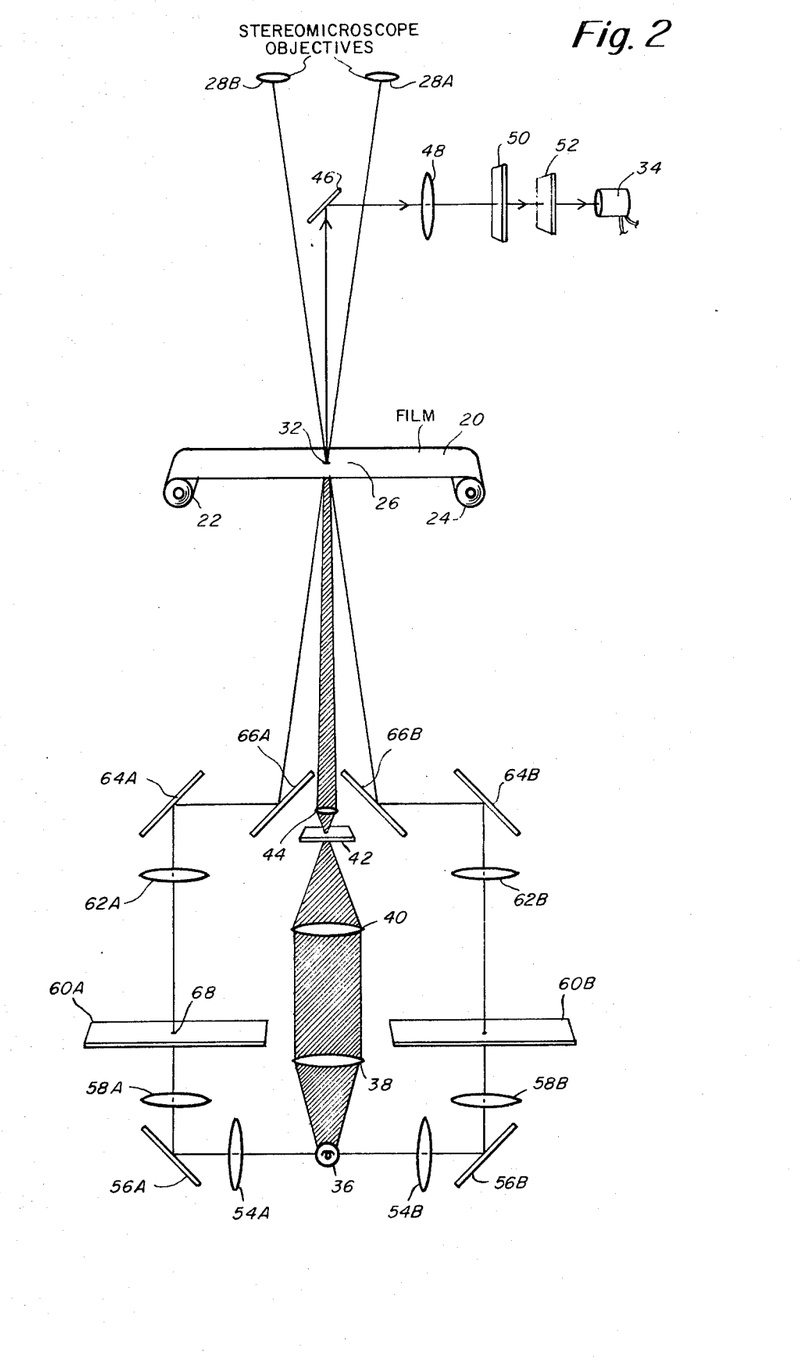
FIG. 2 is a schematic illustration of an optical system for viewing an image frame and for detecting the optical density of predetermined sites on the frame.
Figure 3:
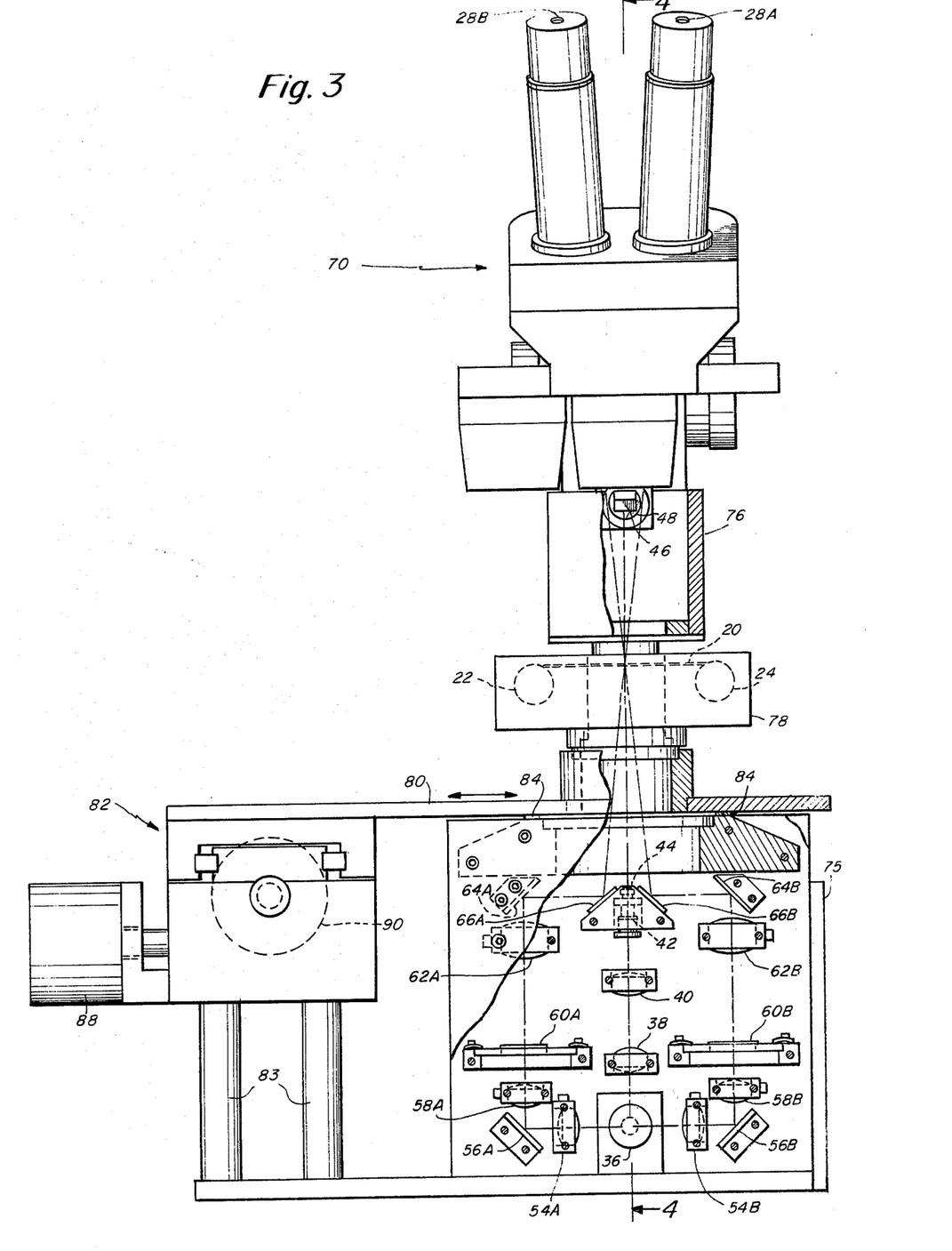
FIG. 3 is a front view, partly broken away, of a device embodying the optical system of FIG. 2.
Figure 4:
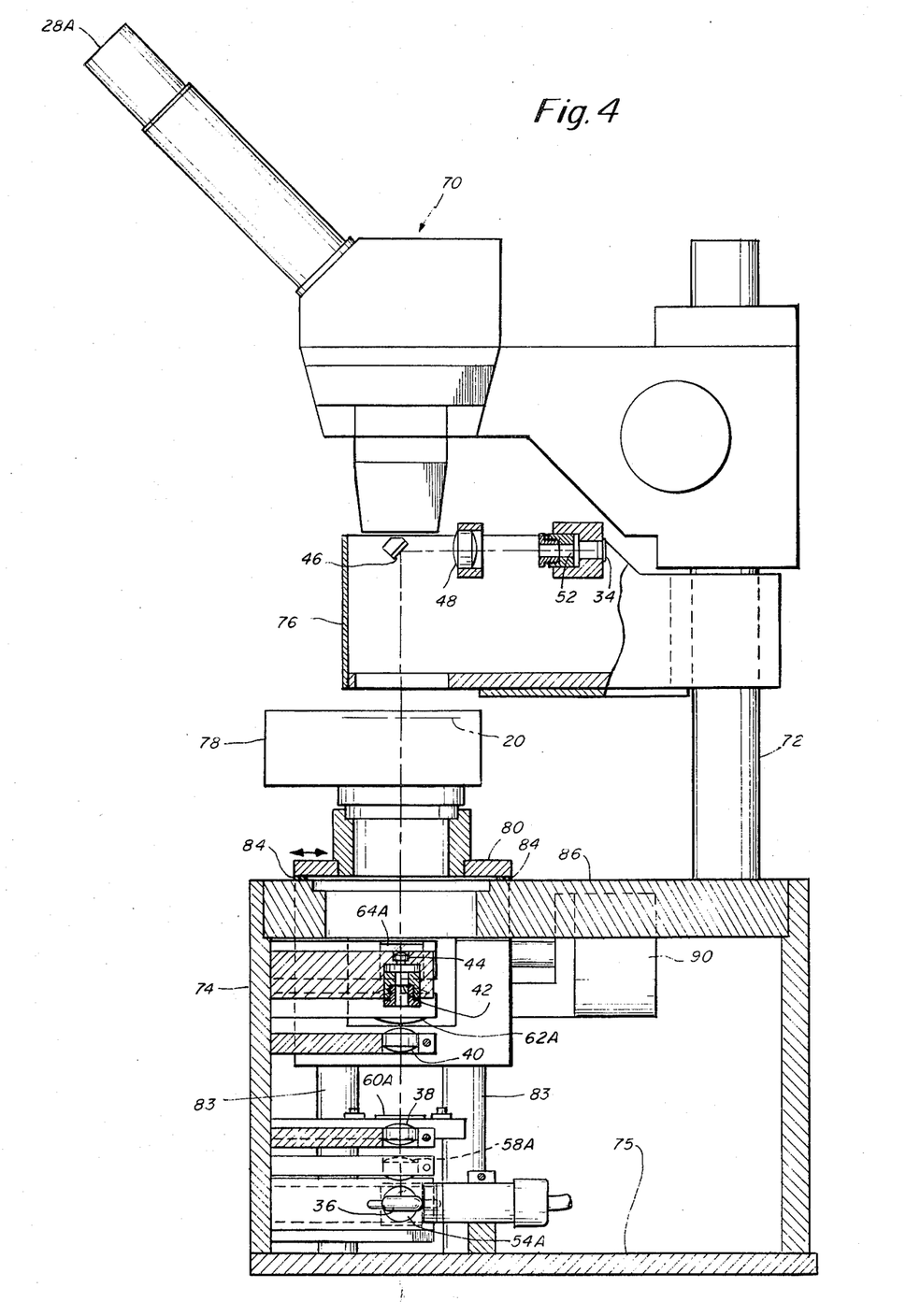
FIG. 4 is a side view, partly broken away, of the device of FIG. 3.

The densitometer optical system used in analyzing the fundus image frames to determine optical density is shown in schematic form in FIG. 2 and in detail in FIGS. 3 and 4. X and Y stepping motors in the system are controlled by the electronic circuitry of FIG. 5.

Figure 5:
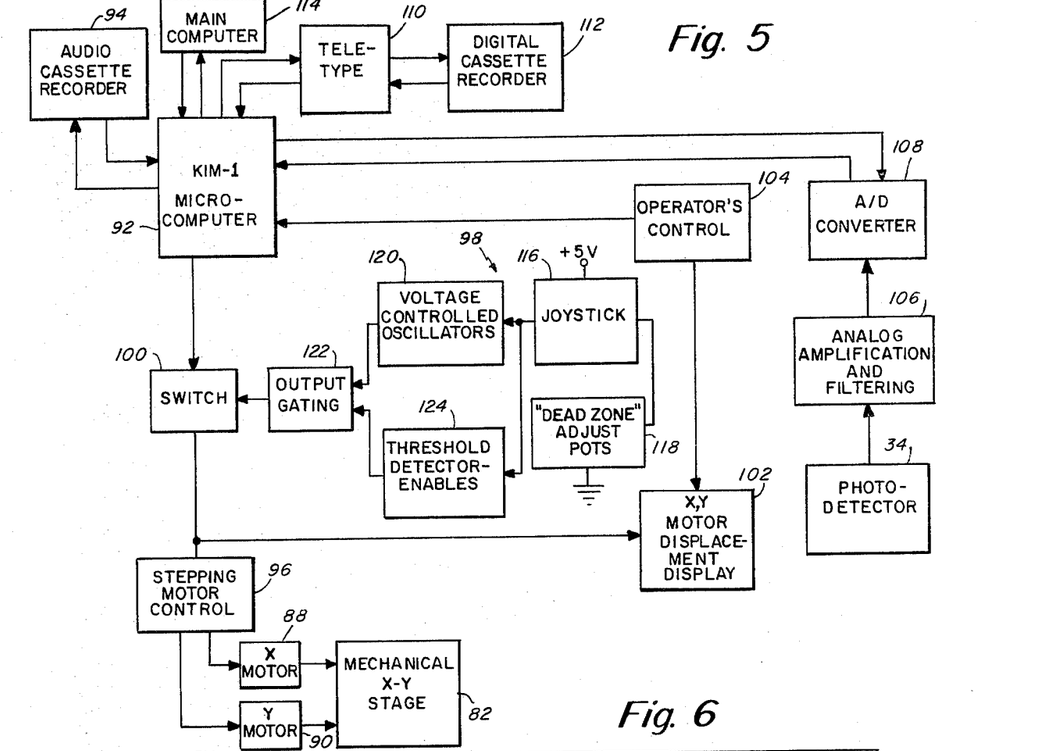
FIG. 5 is a block diagram of the control circuitry and data recording circuitry used in conjunction with the device of FIGS. 2-4.

That circuitry also operates on the signals from the photodetector of the optical system.

As shown in FIG. 2, a film 20 having a series of fundus image frames thereon extends between film rolls 22 and 24. The film rolls are mounted on an X/Y positioning mechanism (FIGS. 3 and 4 discussed below). The optical system includes two subsystems. A viewing subsystem illuminates the entire frame 26 for viewing through the stereomicroscope objectives, or oculars, 28A and 28B. A sensing subsystem illuminates a single image point 32 on the frame 26 and directs the light from that point onto a photodiode 34.

Both optical subsystems are illuminated by a tungsten halogen bulb 36. In the sensing subsystem, light from bulb 36 is directed by condensing lenses 38 and 40 through a pinhole 42. The pinhole is imaged by another lens 44 to form a 200 micrometer diameter image point 32. The light which passes through the film image point is reflected by mirror 46 through a lens 48 and an infrared filter 50. Lens 48 focuses the image point through a pinhole 52 onto the photodiode 34. The output from the photodiode 34 is inversely related to the amount of near infrared light absorbed by the film at the image point and is thus related to the optical density of that image point.

In the film viewing subsystem, light from bulb 36 is directed through left and right optical systems. The left system is designated by the reference letter A and the right system is designated by the reference letter B.

The lenses 54 and 58, separated by mirrors 56, form images of the bulb 36 above blue filters 60. The filters 60 absorb near infrared light. The bulb images above the filters are reimaged onto the objective lenses 28 of the low power stereomicroscope by lenses 62 and mirrors 64 and 66 to provide bright illumination of the film over the 12 mm diameter field of view of the stereomicroscope. Light from the measurement path of the sensing optics is not directed to the objectives 28.

To locate the sensed image point of the film, a set of crosshairs 68 is provided on the left filter 60A. The filter position on the optic axis is adjusted so that the crosshairs are imaged onto the film plane by lens 62A. The crosshairs are aligned with the sensing point 32 by first positioning an opaque spot on a test film such that minimum light transmission is recorded by the photodiode 34. The crosshairs 68 are then aligned with that opaque spot. Thereafter, because only the film is moved, the crosshair is viewed at the image point sensed by the photodiode 34.

A stopband of near infrared light is filtered from the frame illuminating light by filters 60. By providing a photodetector which senses only a passband of light frequencies in the near infrared and by illuminating only the image point by light which includes that passband, the photodetector is not responsive to light reflected, refracted, or scattered from the viewing system. Only the area illuminated by the sensing system affects the signal from photodiode 34.

It is also significant that the sensing light, which includes the near infrared, is imaged onto the film 20 only at the image point 32. With such imaging, there is no danger of sensing scattered light from the outside of the tested image point.

In most cases, the infrared filter 50 may be eliminated because the photodiode itself is frequency selective to the infrared range.

The densitometer optical system of FIG. 2 is shown in detail in FIGS. 3 and 4. The viewer 70, including objectives 28A and 28B, is a conventional low power stereomicroscope mounted to a post 72. The elements of both the viewing subsystem and the sensing subsystem below the film 20 are mounted to the front plate 74 of a lower housing 75. The sensing optics above the film 20 are mounted in an upper housing 76 mounted to the post 72 below the viewer 70. The film is carried in a motorized film pack 78 supported by an X/Y table 80. The table 80 is cantilevered from an X/Y drive mechanism 82 which is in turn supported by legs 83. Under control of an X motor 88 and Y motor 90, the table 80 slides along nylon pads 84 over the top 86 of the lower housing 75. The X/Y mechanism 82 is conventional and in this case is supplied by Instrument Industries of Andover, Mass. It includes two lead-screw-driven linear slides.

The electronic control for the densitometer is shown in FIG. 5. The heart of the system is a KIM-1 microcomputer 92 controlled by programs stored locally in an audiocassette recorder 94. The control 96 of the X/Y drive 82 is signalled by either the microcomputer 92 or a joystick control 98 depending on the position of a switch 100. X and Y movement of the table 80 from a reset position can be monitored by the displacement display 102.

An operator's control panel 104 is provided to feed special instructions to the microcomputer 92 as well as to reset the displacement display. The output signal from photodetector 34 is applied through an amplifier and filter 106 to an analog-to-digital converter 108. The converter is under control of the microcomputer.

Data received from the A/D converter is stored in a digital cassette recorder 112 through a teletype 110. The data can be relayed to an IBM 370 main computer where operations on the data may be carried out.

Figure 6:
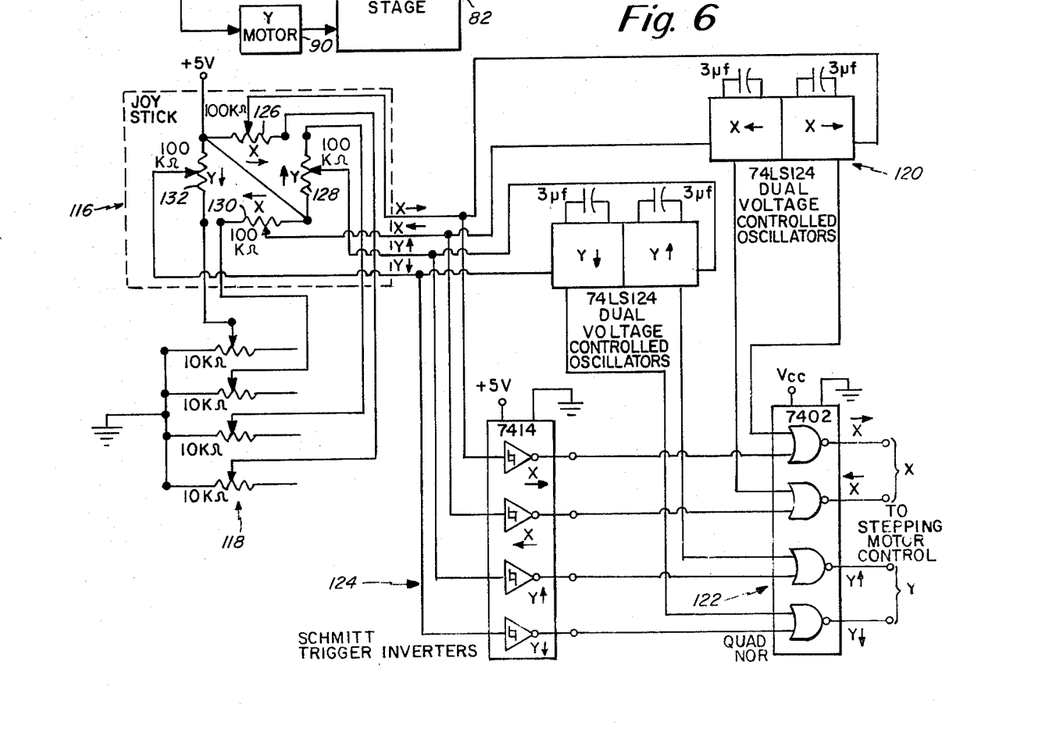
FIG. 6 is a detailed schematic of the joystick control circuitry of FIG. 5.

The joystick control 98 for the X/Y stepping motors, shown in detail in FIG. 6, includes a joystick 116. With movement of the joystick 116, signals from voltage controlled oscillators 120 are gated through gating circuitry 122 by threshold enable circuitry 124. The minimum movement of the joystick which will cause gating by enable circuitry 124 is adjusted by deadzone adjustment pots 118.

The joystick moves the slide contacts on four potentiometers 126, 128, 130, and 132. For example, when the joystick is moved in the positive X and Y directions, the slide contacts on potentiometers 126 and 128 each move toward the five volt line. This increases the voltage applied to the respective voltage controlled oscillators in unit 120 and thus increases the frequency of the oscillator outputs. At the same time, voltages above the threshold voltages of the respective positive X and positive Y Schmitt triggers 124 are applied to those devices. The result is a low input to the positive X and positive Y NOR gates in unit 122 to gate those voltage controlled oscillator outputs through to two of the four motor control lines. Then, during each high output on the positive X motor control line, the X motor is moved one step in the positive direction. Similarly, with each high signal on the oscillating positive Y control line the Y motor moves one step in the positive direction.

By adjusting the four 10 Kohm potentiometers 118, the position of the joystick which results in a threshold voltage being applied to the Schmitt triggers can be set. This permits a dead zone near the center position of the joystick to allow for easy stopping of the X and Y stepping motors.

Use of the above-described system to extract data from a sequence of fundus image frames can now be understood. A roll of, for example, 20 to 30 frames, each including the same fundus image taken at a different instant in time, is positioned in the film pack 78. The film is advanced to a frame which shows the primary blood vessels clearly as in FIG. 1. A convenient starting point is selected. That point should be one which can easily be noted for manual positioning of each frame at that point. With switch 100 positioned for manual control the joystick is operated to move the X/Y table 80 until the crosshairs 68 are positioned at the selected starting point as viewed through objectives 28A and 28B. The X/Y displacement display is then reset so that all future sites can be designated relative to this starting point.

Still under manual control, the joystick is operated to move the film so that the crosshairs are centered at the next selected image point, such as indicated at site 1 in FIG. 1. Once positioned, the displacement indicated on display 102 and a direction can be keyed in through the operator's control to store the image site in memory. Also, a type of scan is keyed into memory. The scan type may, for example, include both direction and length of scan at an image point. Where the image point is at a vessel, the scan should be selected to traverse across the vessel.

As an alternative the control data can be taken directly from the indicator 102 by the microcomputer 92 under command of the operator.

Once each site to be examined has been stored in memory with a scan type, the film is wound to present the first frame at the viewing station. The image frame is positioned with the crosshairs located over the preselected starting point. Then, the switch 100 is switched to automatic control.

Figure 7:
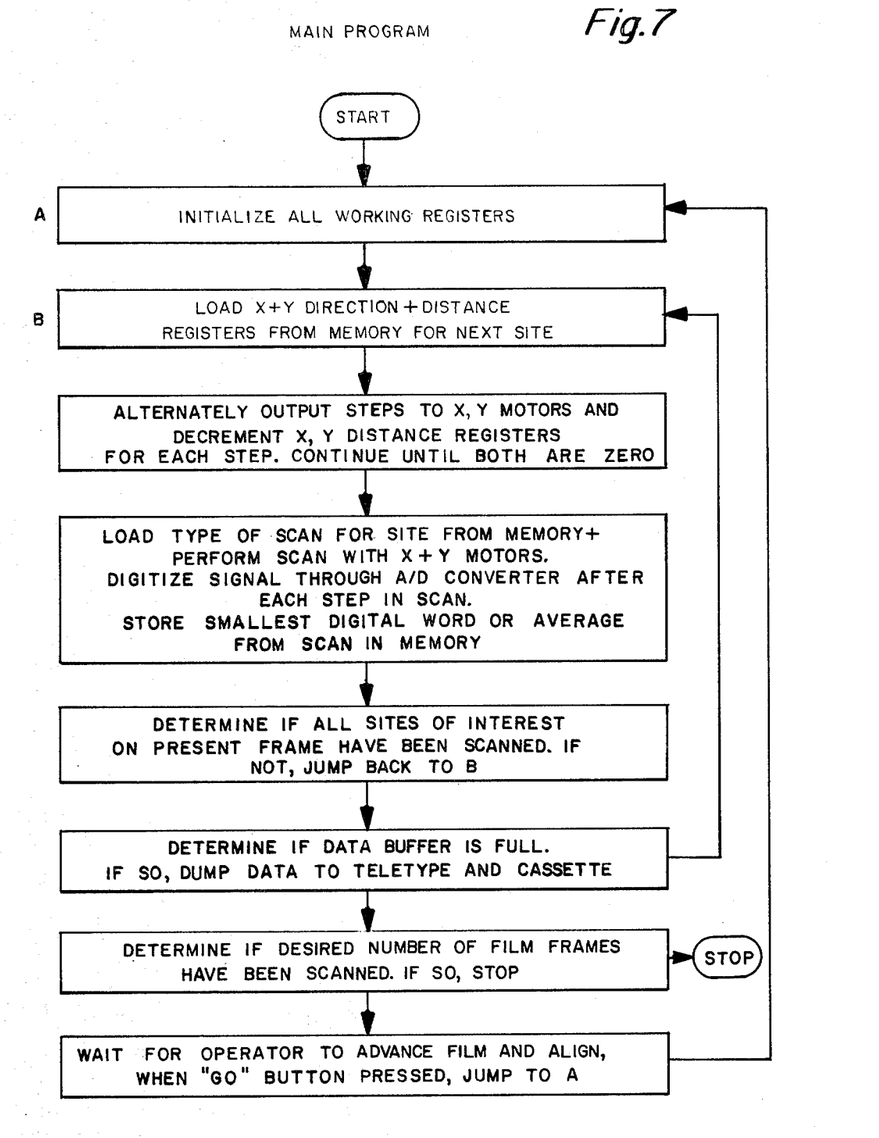
FIG. 7 is a flow chart of a microprocessor program for controlling the X/Y motors in the system of FIGS. 3-5.

Through the operator's control 104, the main program in the microcomputer is started. A flow chart for that program is shown in FIG. 7.

Under the program the working registers are initialized. Then, the X and Y direction and distance registers are loaded from memory for the first site.

Stepping signals are alternately applied to the X and Y stepping motors along the control lines indicated by the direction registers. After each step of a stepping motor the value stored in the respective distance register is reduced by one. The stepping continues until the value in each register is reduced to zero.

Once both registers reach zero, the crosshairs are positioned over the first image site. In order to be certain that all data is taken for the maximum dye concentration across a vessel, the microcomputer now causes the X and Y motors to scan across the vessel. With each step during the scan, the analog signal received from amplifier 106 is digitized by A/D converter 108 under control of the microcomputer. When examining a site over a vessel, the microcomputer selects the smallest digital word received from converter 108 during the scan and stores that value as the datum for that image site. The smallest digital word corresponds to the greatest optical density at the location and thus the greatest dye concentration. If the site is not at a vessel, an average of the detected signals is stored. In the event that the operator notes a flaw in the film he can signal the microcomputer to store zero for that site or frame. The zero is later recognized as an absence of data by the IBM 370 in making computations.

The microcomputer then determines whether any image sites remain to be examined on that frame. If so, it reloads the direction and distance registers for the next site and continues as before to provide the smallest digital word in a scan of that next site.

Once all of the selected image sites have been examined, the microcomputer dumps the data into digital cassette 112 if its own data buffer is full. If there are more frames to be examined on that roll, the microcomputer waits for the operator to move the next frame into position. Alternatively the next frame can be moved into position automatically under control of the digital processor 92. The operator also positions the crosshairs over the starting point using the X/Y control joystick. The operator then presses the GO button in the operator's control 104, and the microcomputer controls X/Y movement and reads the data for each image site on the frame as before. Once all the frames have been examined, the microcomputer stops the process and the film is removed from the filmpack.

Note that the position of the fundus image on the frame is not significant since the starting point is set manually. The image is substantially the same on each frame except that it may be offset as a result of movement of the eye during photographing. Any minor changes in the actual image are accounted for by the scanning procedure which pinpoints the greatest dye concentration at an image site.

Both image site control data and the optical density data are forwarded to the main IBM 370 computer for storage. Each eye has its site information permanently stored on magnetic tape. Thus, rapid sequence image frames from future days can be examined at the very same image sites and the resultant optical density data can be compared. Of course, for future film rolls for the same eye, image site programming is not necessary, that part of the procedure being performed only once for an eye.

The IBM 370 also stores the time at which each frame is photographed. This information is entered manually from the fundus camera timer output.

With each roll of film, it is necessary to calibrate the film and the development process so that a given dye concentration will always result in the same optical density data. To that end, a master 20-step tablet is contact printed onto unexposed film from the same emulsion lot as the angiogram film to produce a step wedge for each roll of rapid sequence film. The step wedge is developed along with the angiogram and can then serve as an optical density reference.

Figure 8:
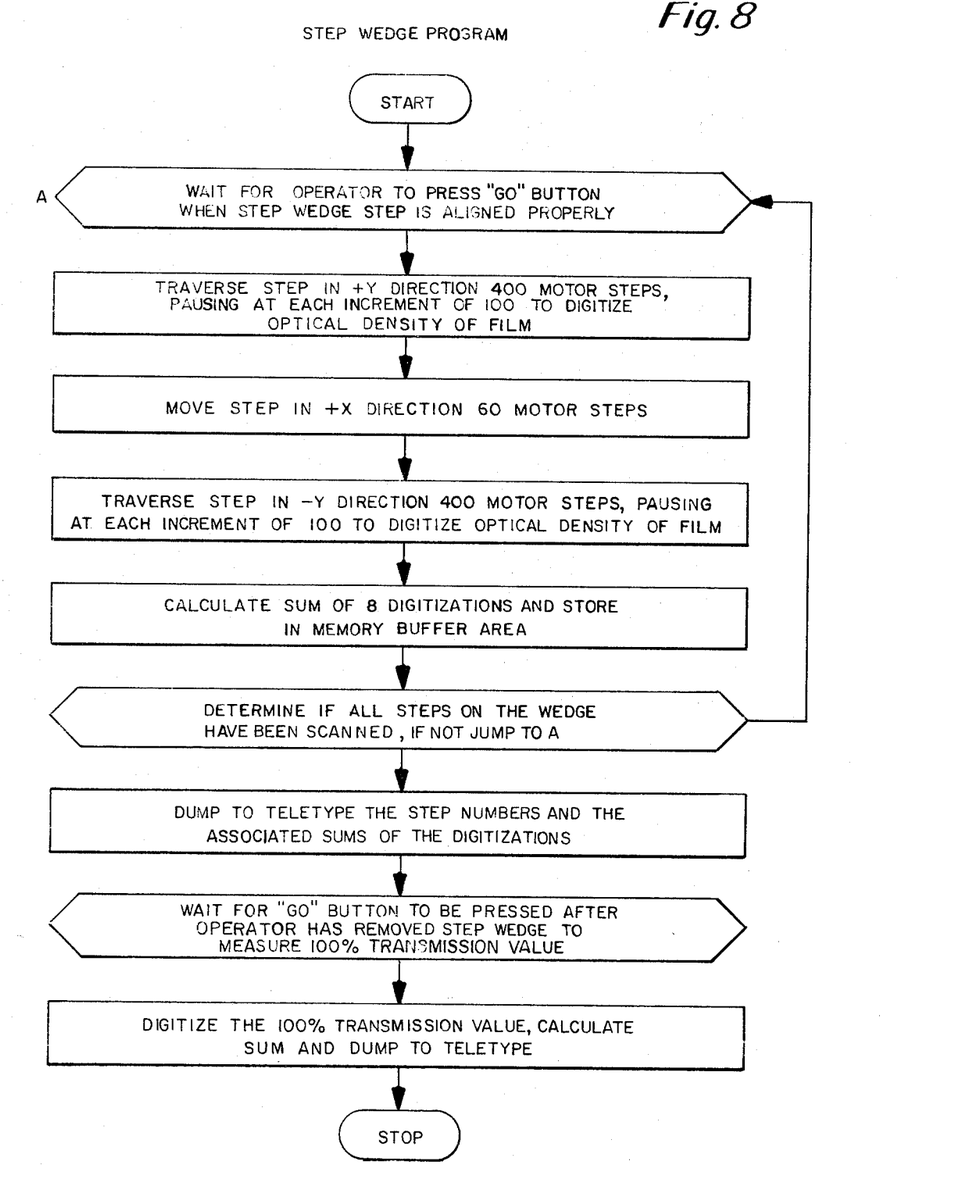
FIG. 8 is a flow chart for a microprocessor program for calibrating the film density measurement.

The reference provided by the step wedge can be read into the microcomputer under control of the program of FIG. 8. The operator positions each step on the wedge over the crosshairs and the microcomputer controls the scan and makes the necessary readings. Later the IBM 370 computer makes the necessary calculations. Each reading from the angiogram and from the step wedge is divided by the light sensed through a clear aperture to produce optical transmission measurements T. From the step wedge measurements, the IBM 370 can provide a table of log T against the logarithm of the light intensity which exposed each step of the step wedge through the master 20-step tablet. From the log T of each site of the angiogram the logarithm of fluorescent intensity for that site can then be interpolated from the table.

From the fluorescent intensity information, the IBM 370 can reconstruct the time course of fluorescent intensity at each of the selected sites on the fundus. These curves represent the dilution of the injected bolus of fluorescein dye as undyed blood enters the heart; the curves are thus known as dye dilution curves. Each curve rises rapidly to a peak as dye enters tissue below the measurement site, decays approximately exponentially as the bolus is diluted, and rises and falls again as dye recirculates to the heart from tissues closer to it than the eye. The rises after the first are known as recirculation humps.

The shape of the dye dilution curve is the same in all arteries leading to the eye. Its position along the time axis at a given site of the ocular fundus depends upon the time it takes dyed blood to reach that site. A large part of this time is spent traveling to the eye, and this part is the same for all sites. The remainder of the time depends upon the average velocity of blood flow within the eye. It is this latter component in some parts of the eye, the filling delay, which is sensitive to perfusion pressure. In order to focus attention on the filling delay the heart-to-eye time is subtracted from all measurements. Since the circulation of the retina is relatively unaffected by moderate elevations of intraocular pressure, the time of occurrence of the dye dilution curve at a central retinal artery site, $t_{cra}$, is taken as the heart-to-eye time.

The time of peak dye fluorescence in a dye dilution curve at a measurement site is taken as the time of arrival of the dye bolus at the site. Because the peak time is not usually concurrent with exposure during the rapid sequence photography, it is necessary to fit the experimental data points to a mathematical model and to then take a peak time from that model. To that end, the IBM 370 is programmed to make use of a modified Fletcher-Powell steepest descent method of curve fitting.

To understand the computer program, it should be recognized that the dye dilution curves have the mathematical form of the following equation:

$$I_p(t) = X_1(t-X_4)^{X_2} e^{-X_3(t-x_4)} \tag{2}$$

where $I_p(t)$ is the fluorescent intensity as a function of time. The objective of curve fitting is to find the set of parameters $X_1, X_2, X_3$ and $X_4$ which minimize the differences between the model curve defined by equation 2 and the data.

By using log I data in the curve fitting, equation 2 can be placed in the form:

$$\log I_p = \log x_1 + x_2 \log(t-x_4) - (x_3 \log e)(t-x_4) \tag{3}$$

For notational convenience, define y and $y_p$ as follows:

$$y = \log I$$

$$y_p = \log I_p$$

The error to minimize is then:

$$E = \frac{1}{N} \sum_{i=1}^{N} [y(t_i) - y_p(t_i)]^2 \tag{4}$$

where $y(t_i)$ are the data points and $y_p(t_i)$ are the predicted values. The Fletcher-Powell steepest descent method (Computer Journal, 6, p 163, 1963) can be used to find the parameters which give the minimum error. However, since the error is not a smooth function of the parameters, that method occasionally takes many iterations to find the minimum error.

To avoid the extensive iterations, the regression method for linear curve fitting is used to provide initial estimates of $X_1, X_2, X_3$ and $X_4$. To that end, it is recognized that equation 3 has the form of a multiple regression line:

$$y_p = \log X_1 + X_2 Z_1 + (X_3 \log e) Z_2 \tag{5}$$

$$= \text{intercept} + R_1 Z_1 + R_2 Z_2$$

where $R_1$ and $R_2$ are the regression coefficients and where:

$$Z_1 = \log(t - X_4)$$

$$Z_2 = t - X_4$$

To first obtain a reasonable estimate of $X_4$, a straight line is fit to the rising portion of the dye dilution curve, I(t); and $X_4$ is defined as the time at which the line intersects the time axis. From that value the values of $Z_1$ and $Z_2$ are calculated for each $t_i$, and standard regression method statistical techniques are used to find the coefficients of equation 5. These coefficients are converted to estimates of $X_1, X_2$, and $X_3$ as follows:

$$X_1 = 10^{intercept}$$

$$X_2 = R_1$$

$$X_3 = R_2/\log e$$

These parameters are nearly optimum and are used as the starting point of 200 iterations of the steepest descent method to determine the final parameter estimates. The time at which the peak of the dilution curve occurs is then calculated using the final parameter estimates by setting the time derivative of equation 2 equal to zero and solving for t. This results in:

$$t_p = X_4 + X_2/X_3$$

The curve fitting procedure discussed above is applied to data from a site located over a branch of the central retinal artery to produce $t_{cra}$ and from sites on the optic disc and peripapillary choroid to produce $t_p$. Those are then converted to filling delay by equation 1. The filling delays are the basic indicators of changes in optic disc circulation and thus of the likelihood of resultant blindness.

While the invention has been particularly shown and described with reference to a preferred embodiment thereof, it will be understood by those skilled in the art that various changes in form and details may be made therein without departing from the spirit and scope of the invention as defined by the appended claims. For example, the system may be controlled by hardwired circuitry rather than by the microcomputer software. Also, certain aspects of the invention have applicability to the analysis of television images as well as film images. Further, relative movement between the image frame and the intensity sensing system may be due to movement of the latter rather than of the image frame.

I claim:

1. A film analysis system for determining the optical density of an image on successive film frames at the same preselected image sites, the image position on the frames being subject to change from frame to frame, the system comprising:

a film carrier;

a sensing optical system for illuminating a film on the carrier and for projecting the light from an illuminated point onto a photodetector;

drive means for providing relative movement between the sensing optical system and the film carrier to illuminate selected points on the film; and drive control means, including a control data memory, for controlling automatic relative movement of the sensing optical system and the film carrier from an initial film position to subsequent positions in accordance with stored position control data to successively illuminate preselected image sites.

2. A film analysis system as claimed in claim 1 wherein the drive conrol means also controls a short scanning movement between the sensing optical system and the film carrier at each image site.

3. A film analysis system as claimed in claim 2 further comprising a data memory for storing minimum or maximum values of the photodetector output during scans.

4. A film analysis system as claimed in claim 1 wherein the drive means provides for rectilinear movement in orthogonal X and Y directions.

5. A film analysis system as claimed in claim 4 wherein the drive means includes X and Y stepping motors.

6. A film analysis system as claimed in claim 5 wherein the drive control means further comprises manual control for positioning the film carrier at an initial position.

7. A film analysis system as claimed in claim 1 wherein the drive control means includes a digital processor.

8. A film analysis system as claimed in claim 1 wherein the photodetector detects a passband of light frequencies and further comprising:

a viewer optical system for illuminating the image on the film and for directing the image illuminating light from the film to the viewer, the viewer optical system including an optical filter ahead of the film for filtering a stopband of frequencies from the image illuminating light, the stopband coinciding with the photodetector passband.

9. A film analysis system for viewing an image on a film while determining the optical density of an image point comprising:

a detector for detecting a passband of light frequencies;

a viewer for viewing the image on the film;

a sensing optical system for illuminating the image point on the film and for directing the point illuminating light from the image point to the detector;

a viewer optical system for illuminating the image on the film and for directing the image illuminating light from the film to the viewer, the viewer optical system including an optical filter ahead of the film for filtering a stopband of frequencies from the image illuminating light, the stopband coinciding with the detector passband.

10. A film analysis system as claimed in claim 8 or 9 wherein the viewer optical system includes an image point indicator.

11. An film analysis system as claimed in claim 10 wherein the image point indicator is a pair of crosshairs on the optical filter.

12. A method of determining the optical density of a recorded image at preselected image sites for successive instants in time comprising:

providing a plurality of image frames, each taken as a known instant in time;

positioning each image frame relative to a density sensing system at a predetermined starting position of the image;

moving each image frame and the density sensing system relative to each other under electronic control to predetermined image sites in accordance with stored position control data; and sensing the image density at each image site.

13. A method of determining the optical density of a recorded image as claimed in claim 12 wherein the image is recorded on film.

14. A method of determining the optical density of a recorded image as claimed in claim 12 further comprising the step of moving each image frame and the density sensing system relative to each other in a short scan at each of the image sites.

15. A method of determining the optical density of a recorded image as claimed in claim 14 further comprising the step of selecting the minimum or maximum image density during the scan at an image site.

16. A method of determining the optical density of a recorded image as claimed in claim 12 wherein each image frame is positioned relative to the density sensing system at the starting position under manual control.

17. A method of determining the optical density of a recorded image as claimed in claim 12 wherein the electronic control is provided by a digital processor.

* * * * *